US00PP29152P2

(12) United States Plant Patent
Smith et al.

(10) Patent No.: US PP29,152 P2
(45) Date of Patent: Mar. 27, 2018

(54) DENDRANTHEMA PLANT NAMED 'HARVEST IGLOO'

(50) Latin Name: *Chrysanthemum×morifolium*
Varietal Denomination: Harvest Igloo

(71) Applicants: Mark A. Smith, Fort Myers, FL (US); Cornelis P. Vandenberg, Fort Myers, FL (US)

(72) Inventors: Mark A. Smith, Fort Myers, FL (US); Cornelis P. Vandenberg, Fort Myers, FL (US)

(73) Assignee: Aris Horticulture, Inc., Barberton, OH (US)

( * ) Notice: Subject to any disclaimer, the term of this patent is extended or adjusted under 35 U.S.C. 154(b) by 0 days.

(21) Appl. No.: 15/530,073

(22) Filed: Nov. 30, 2016

(51) Int. Cl.
*A01H 5/02* (2018.01)

(52) U.S. Cl.
USPC ..... Plt./296

(58) Field of Classification Search
USPC ..... Plt./286, 296
See application file for complete search history.

*Primary Examiner* — Susan McCormick Ewoldt
(74) *Attorney, Agent, or Firm* — C. A. Whealy

(57) ABSTRACT

A new and distinct cultivar of Dendranthema plant named 'Harvest Igloo', characterized by its upright, outwardly spreading and uniformly mounded plant habit; freely branching habit; dense and full plant form; uniform and freely flowering habit; decorative-type inflorescences; bronze-colored ray florets; natural season flowering occurs about September 13 to 18 in Pennsylvania; and good garden performance and winter hardiness.

2 Drawing Sheets

Botanical designation: *Chrysanthemum×morifolium.*
Cultivar denomination: 'HARVEST IGLOO'.

BACKGROUND OF THE INVENTION

The present invention relates to a new and distinct Dendranthema plant, botanically known as *Chrysanthemum×morifolium*, commercially grown as a perennial garden-type Dendranthema plant, and hereinafter referred to by the cultivar name 'Harvest Igloo'.

The new Dendranthema is the product of a planned breeding program conducted by the Inventors in Bogota, Colombia and Smoketown, Pa. The objective of the breeding program is to create new perennial garden-type Dendranthema plants having uniformly mounding plant habit, inflorescences with desirable inflorescence forms, attractive ray and disc floret shapes and colors, winter hardiness and good garden performance.

The new Dendranthema plant originated from a cross-pollination made by the Inventors in 2008 in Bogota, Colombia, of a proprietary selection of *Chrysanthemum×morifolium* identified as code number N0695, not patented, as the female, or seed, parent with *Chrysanthemum×morifolium* 'Cool Yoigloo', disclosed in U.S. Plant Pat. No. 20,225, as the male, or pollen, parent. The new Dendranthema plant was discovered and selected by the Inventors as a single flowering plant within the progeny of the stated cross-pollination in a controlled greenhouse environment in Smoketown, Pa. on Sep. 27, 2012.

Asexual reproduction of the new Dendranthema plant by vegetative terminal cuttings was first conducted in a controlled greenhouse environment in Smoketown, Pa. in March, 2013 and such asexual propagation has shown that the unique features of this new Dendranthema plant are stable and reproduced true to type in successive generations.

SUMMARY OF THE INVENTION

Plants of the new Dendranthema have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Harvest Igloo'. These characteristics in combination distinguish 'Harvest Igloo' as a new and distinct garden-type Dendranthema plant:

1. Upright, outwardly spreading and uniformly mounded plant habit.
2. Freely branching habit; dense and full plant form.
3. Uniform and freely flowering habit.
4. Decorative-type inflorescences.
5. Bronze-colored ray florets.
6. Natural season flowering occurs about September 13 to 18 in Pennsylvania.
7. Good garden performance and winter hardiness.

In side-by-side comparisons, plants of the new Dendranthema differ from plants of the female parent selection primarily in inflorescence form and ray floret color as plants of the female parent selection have daisy-type inflorescences with pink-colored ray florets. In addition, plants of the new Dendranthema have larger inflorescences than plants of the female parent selection.

In side-by-side comparisons, plants of the new Dendranthema differ from plants of the male parent, 'Cool Yoigloo', primarily in ray floret color as plants of 'Cool Yoigloo' have bright red purple-colored ray florets. In addition, plants of the new Dendranthema have larger inflorescences and flower earlier than plants of 'Cool Yoigloo'.

Plants of the new Dendranthema can be compared to plants of *Chrysanthemum×morifolium* 'Warm Yoigloo', disclosed in U.S. Plant Pat. No. 19,168. In side-by-side comparisons, plants of the new Dendranthema differ from plants of 'Warm Yoigloo' in the following characteristics:

1. When grown under natural season conditions, plants of the new Dendranthema flower earlier than plants of 'Warm Yoigloo'.
2. Ray florets of plants of the new Dendranthema are brighter in color than ray florets of plants of 'Warm Yoigloo'.
3. Inflorescences of plants of the new Dendranthema last longer than inflorescences of plants of 'Warm Yoigloo'.

BRIEF DESCRIPTION OF THE PHOTOGRAPHS

The accompanying photographs illustrate the overall appearance of the new Dendranthema showing the colors as true as it is reasonably possible to obtain in colored reproductions of this type. Colors in the photographs may differ slightly from the color values cited in the detailed botanical description which accurately describe the colors of the new Dendranthema plant.

The photograph on the first sheet comprises a top perspective view of a typical flowering plant of 'Harvest Igloo' grown in a container.

The photograph on the second sheet is a close-up view of a typical flowering plant of 'Harvest Igloo'.

DETAILED BOTANICAL DESCRIPTION

The aforementioned photographs and following observations and measurements describe plants grown during the early autumn in 25-cm containers in an outdoor nursery in Lancaster, Pa. and under cultural practices typical of commercial garden-type Dendranthema production. During the production of the plants, day temperatures averaged 26.7° C. and night temperatures ranged from 15.6° C. to 18.3° C. Plants were five months old when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Harvest Igloo'.

Parentage:

*Female, or seed, parent.*—Proprietary selection of *Chrysanthemum×morifolium* identified as code number N0695, not patented.

*Male, or pollen, parent.*—*Chrysanthemum×morifolium* 'Cool Yoigloo', disclosed in U.S. Plant Pat. No. 20,225.

Propagation:

*Type.*—Vegetative terminal cuttings.

*Time to initiate roots, summer and winter.*—About two weeks.

*Root description.*—Fine, fibrous; typically white in color, actual color of the roots is dependent on substrate composition, water quality, fertilizer type and formulation, substrate temperature and physiological age of roots.

*Rooting habit.*—Freely branching, dense.

Plant description:

*Plant and growth habit.*—Perennial garden-type Dendranthema plant with decorative-type inflorescences; upright, outwardly spreading and uniformly mounding plant habit; strong and vigorous growth habit.

*Branching habit.*—Freely branching habit, primary lateral branches developing at potentially every node, each primary lateral with multiple secondary and tertiary branches; dense and full plant form; pinching is not required.

*Plant height.*—About 35 cm.

*Plant width.*—About 54 cm.

*Lateral branches.*—Length: About 36 cm. Diameter: About 5 mm. Internode length: About 2.5 cm. Strength: Strong. Aspect: Upright to curving upright. Texture: Pubescent, minute; longitudinally ridged. Color: Close to 144A.

*Leaves.*—Arrangement: Alternate, simple. Length: About 3.2 cm. Width: About 2.5 cm. Shape: Ovate. Apex: Cuspidate. Base: Truncate to attenuate. Margin: Palmately lobed, sinuses between lateral lobes mostly divergent. Texture, upper and lower surfaces: Pubescent, minute; veins prominent on lower surface. Venation pattern: Pinnate. Color: Developing and fully expanded leaves, upper surface: More green than 147A; venation, close to 146A. Developing and fully expanded leaves, lower surface: Close to between 147B and 146A; venation, close to 146A. Petioles: Length: About 5 mm. Diameter: About 3.5 mm. Texture, upper and lower surfaces: Pubescent; minute. Color, upper surface: Close to 146A. Color, lower surface: Close to 146A to 146B.

Inflorescence description:

*Type and arrangement.*—Decorative-type inflorescence form with elongated oblong-shaped ray florets; disc and ray florets arranged acropetally on a capitulum; inflorescences face mostly upright and held above and beyond the foliar plane on strong peduncles.

*Fragrance.*—None detected.

*Flowering response.*—Under natural season conditions, plants flower about September 13 to 18 in Pennsylvania.

*Postproduction longevity.*—Inflorescences maintain good color and substance for about three to six weeks on the plant depending on temperatures; inflorescences persistent.

*Quantity of inflorescences.*—Freely flowering habit with numerous inflorescences developing per lateral branch.

*Inflorescence buds.*—Height: About 6 mm. Diameter: About 7 mm. Shape: Oblate. Color: Close to between 147A and 146A.

*Inflorescence size.*—Diameter: About 3.5 cm. Depth (height): About 1.5 cm. Disc diameter: If present, about 4 mm. Receptacle diameter: About 5 mm. Receptacle height: About 6 mm.

*Receptacle color.*—Close to 144B.

*Ray florets.*—Quantity and arrangement: About 125 ray florets develop per inflorescence and arranged in eight to nine whorls. Length: About 1.7 cm. Width: About 5 mm. Shape: Elongated oblong. Apex: Obtuse; occasionally, emarginate. Base: Attenuate and then fused into a short tube. Margin: Entire. Orientation: Initially upright, then horizontal. Texture, upper and lower surfaces: Smooth, glabrous; longitudinally ribbed. Color: When opening, upper surface: Close to between 162A and 163A; with development, becoming overlain with close to 183A to 183B; at the base, close to 144A. When opening, lower surface: Close to 9C; with development, becoming overlain with close to 183A to 183B. Fully opened, upper surface: Close to 169A becoming increasingly overlain with close to 183A; at the base, close to 144A; color becoming closer to 183A with development. Fully opened, lower surface: Close to 9B to 9C becoming increasingly overlain with close to 183B to 183C; color becoming closer to 183B to 183C with development.

*Disc florets*.—Quantity and arrangement: If present, about 1 to 24 fused disc florets develop per inflorescence and massed at the center of the capitulum. Length: About 3.5 mm. Diameter: About 1 mm. Shape: Tubular, elongated. Apex: Five-pointed. Texture, inner and outer surfaces: Smooth, glabrous. Color, mature: Apex: Close to 12A. Mid-section: Close to 144A. Base: Close to NN155D.

*Phyllaries*.—Quantity and arrangement: About 12 to 18 phyllaries develop per inflorescence and arranged in about one to two whorls. Length: About 6 mm. Width: About 2.5 mm. Shape: Lanceolate. Apex: Acute. Base: Truncate. Margin: Entire; membraneous. Texture, upper surface: Smooth, glabrous. Texture, lower surface: Pubescent, minute. Color, upper surface: Close to 146A. Color, lower surface: Close to between 147A and 146A.

*Peduncles*.—Length, terminal peduncle: About 5.5 cm. Length, third peduncle: About 7.5 cm. Diameter, terminal peduncle: About 2 mm. Angle: Mostly upright or curving upright. Strength: Strong, wiry. Texture: Pubescent; minute. Color: Close to 146A.

*Reproductive organs*.—Androecium (present on disc florets only): Stamen number: Five per floret. Filament length: About 4 mm. Filament color: Close to 150D. Anther length: Less than 1 mm. Anther shape: Narrowly oblong. Anther color: Close to 12A. Pollen amount: None observed. Gynoecium (present on ray and disc florets): Pistil length: About 5 mm. Stigma shape: Bi-parted. Stigma color: Close to 9A. Style length: About 4 mm. Style color: Close to 9A. Ovary color: Close to 145D.

*Seeds and fruits*.—Seed and fruit production has not been observed on plants of the new Dendranthema.

Disease & pest resistance: Resistance to pathogens and pests common to Dendranthema plants has not been observed on plants of the new Dendranthema grown under commercial production conditions.

Garden performance & temperature tolerance: Plants of the new Dendranthema have demonstrated excellent garden performance, are hardy to USDA Zone 5 and tolerate high temperatures about 37.8° C.

It is claimed:

1. A new and distinct Dendranthema plant named 'Harvest Igloo' as illustrated and described.

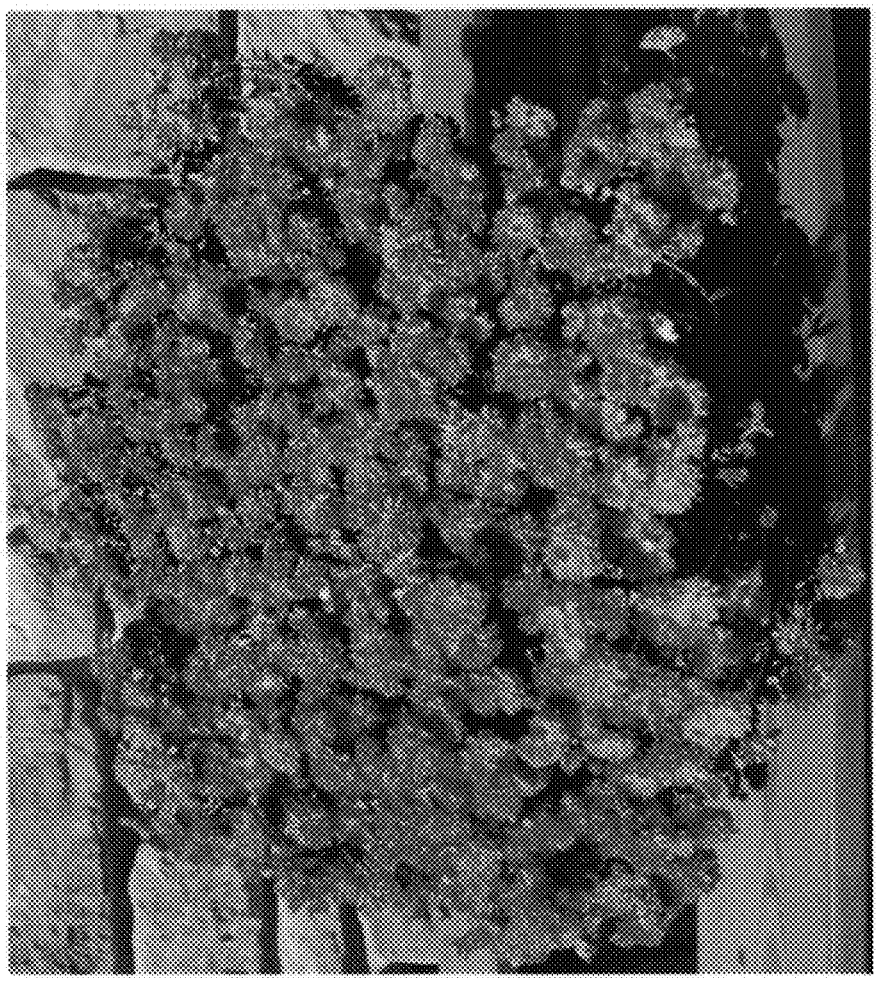

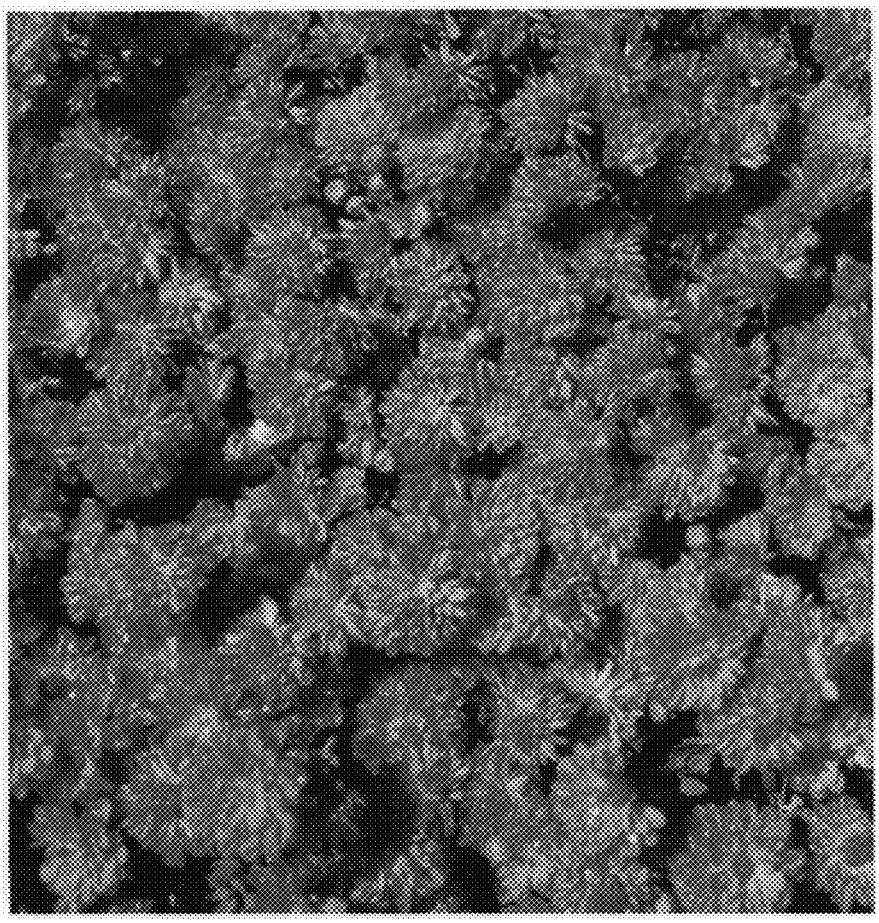

* * * * *